US011696966B1

(12) United States Patent
Jackson et al.

(10) Patent No.: US 11,696,966 B1
(45) Date of Patent: Jul. 11, 2023

(54) DISINFECTANT FOG DISPENSER SYSTEM

(71) Applicants: Darcy Jackson, Fort Lauderdale, FL (US); Darryl Rhue, Fort Lauderdale, FL (US); Little Rhue, Fort Lauderdale, FL (US)

(72) Inventors: Darcy Jackson, Fort Lauderdale, FL (US); Darryl Rhue, Fort Lauderdale, FL (US); Little Rhue, Fort Lauderdale, FL (US)

(*) Notice: Subject to any disclaimer, the term of this patent is extended or adjusted under 35 U.S.C. 154(b) by 238 days.

(21) Appl. No.: 17/123,456

(22) Filed: Dec. 16, 2020

(51) Int. Cl.
| | | |
|---|---|---|
| *A61L 2/22* | (2006.01) | |
| *A61L 2/23* | (2006.01) | |
| *A61L 101/02* | (2006.01) | |
| *A61L 101/36* | (2006.01) | |
| *A61L 101/06* | (2006.01) | |
| *A61L 101/44* | (2006.01) | |
| *A61L 101/32* | (2006.01) | |

(52) U.S. Cl.
CPC .............. *A61L 2/22* (2013.01); *A61L 2/23* (2013.01); *A61L 2101/02* (2020.08); *A61L 2101/06* (2020.08); *A61L 2101/32* (2020.08); *A61L 2101/36* (2020.08); *A61L 2101/44* (2020.08); *A61L 2202/15* (2013.01); *A61L 2202/25* (2013.01)

(58) Field of Classification Search
None
See application file for complete search history.

(56) References Cited

U.S. PATENT DOCUMENTS

| 4,235,373 A * | 11/1980 | Clark .................. B65D 83/262 239/34 |
|---|---|---|
| 2005/0224596 A1* | 10/2005 | Panopoulos .......... A01M 25/00 239/722 |
| 2008/0156896 A1* | 7/2008 | Anderson ............ B65D 83/262 239/34 |
| 2008/0223953 A1* | 9/2008 | Tomono ............... A61M 11/042 128/200.16 |
| 2011/0073675 A1* | 3/2011 | Wolosuk .................. A61L 9/14 239/210 |

(Continued)

OTHER PUBLICATIONS

Ecolab.com—A Supplement to Get the FAQs: Disinfectants in the Fight Against COVID-19. Webinar [online] [retrieved Oct. 5, 2022] https://www.ecolab.com/-/media/Widen/Healthcare/EcolabWebinarDisinfectantsCOVIDFAQ042920pdf.pdf (Year: 2020).*

(Continued)

*Primary Examiner* — Jelitza M Perez
(74) *Attorney, Agent, or Firm* — Sanchelima & Associates, P.A.; Christian Sanchelima; Jesus Sanchelima

(57) ABSTRACT

A disinfectant fog dispensing container and system includes a cylindrical container and a transparent widow for viewing the amount of fluid in the container. The container further includes a fill port on the side of the container. The fill port provides access to an interior of the container and allows the user to fill the container with fluid therein which will then be dispensed as fog. Additionally, the system includes a battery powered rotating base wherein the container will rotate and dispense the contents of the container in an enclosed area. The enclosed area may include locations such as a living room, a classroom, or a vehicle.

9 Claims, 3 Drawing Sheets

(56) References Cited

U.S. PATENT DOCUMENTS

2013/0026181 A1* 1/2013 Carpenter ............... B05B 12/12
                                                      222/52
2015/0246150 A1* 9/2015 De Koster .............. A61L 2/186
                                                      435/264

OTHER PUBLICATIONS

US-EPA: Memorandum-Efficacy Review for 777-99, BRACE, [online] [retrieved on Oct. 5, 2022], pp. 1-9. https://www3.epa.gov/pesticides/chem_search/cleared_reviews/csr_PC-001501_29-Sep-10_a.pdf (Year: 2010).*

Amazon.com—Fuel Filler Door Gas Tank Cap Fuel Door Port Pot Flap Hinge Cover. [online] [retrieved on Oct. 5, 2022], pp. 1-2. https://www.amazon.co.uk/Filler-Hinge-51177069449-Replacement-2003%E2%80%912012/dp/B08J49P1MQ (Year: 2020).*

Merriam-Webster Dictionary—"Hermetically" definition. [online] [retrieved on Jan. 13, 2023]. pp. 1-3 https://www.merriam-webster.com/dictionary/hermetically (Year: 2023).*

\* cited by examiner

DISINFECTANT FOG DISPENSER SYSTEM

BACKGROUND OF THE INVENTION

1. Field of the Invention

The present invention relates to disinfecting fogger machine and, more particularly, to a rotating room disinfecting fogger that includes a cylindrical container and a battery powered rotating base to dispense the contents of the container in a closed area.

2. Description of the Related Art

Several designs for a disinfecting fogger have been designed in the past. None of them, however, include a disinfectant fog dispensing can and system which includes a cylindrical container and a transparent widow for viewing the amount of fluid in the container. The container further includes a fill port on the side of the container. The fill port provides access to an interior of the container and allows the user to fill the container with fluid therein which will then be dispensed as fog. Additionally, the system includes a battery powered rotating base wherein the container will rotate and dispense the contents of the container in an enclosed area. The enclosed area may include locations such as a living room, a classroom, or a vehicle. It is known that due to the spread of infections and diseases such as Covid-19 there is a need to thoroughly disinfect an enclosed area. Therefore, there is a need for a disinfecting rotating fogger for user to easily and efficiently disinfect their enclosed areas.

Applicant believes that a related reference corresponds to U.S. Pat. No. 8,608,032 issued for a motorized, rotating aerosol dispensing apparatus. Applicant believes that another related reference corresponds to U.S. Pat. No. 8,889,081 issued for a machine for dispensing a disinfecting spray into an enclosed room. However, the cited references differ from the present invention because they fail to disclose a disinfectant fog dispensing system that includes a cylindrical container with a transparent window and a fill port. Additionally, the references fail to disclose a battery powered rotating base.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a disinfectant fog dispensing system which easily and efficiently disinfects an enclosed area by releasing a disinfectant fog.

It is another object of this invention to provide a disinfectant fog dispensing system which includes a fill port to allow the system to be continuously refilled and supplied with disinfectant thereby increasing its period of use.

It is still another object of the present invention to provide a disinfectant fog dispensing system that releases fog at predetermined intervals to continuously maintain an enclosed area in a disinfected state.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
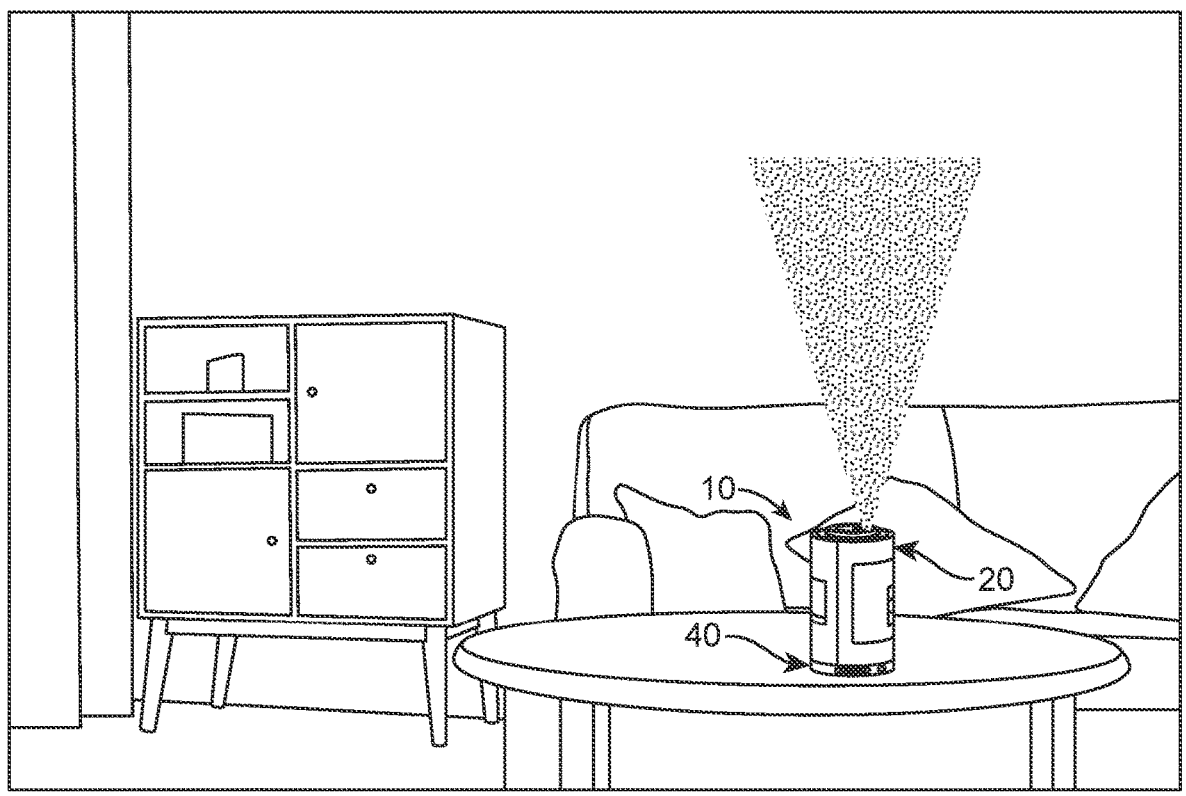
FIG. 1 represents an operational isometric view of room disinfecting fogger system 10 disinfecting an enclosed space in accordance to an embodiment of the present invention.

Referring now to the drawings, where the present invention is generally referred to with numeral 10, it can be observed a disinfectant fog dispensing system 10 that basically includes a container assembly 20 and a base assembly 40.

Figure 2:
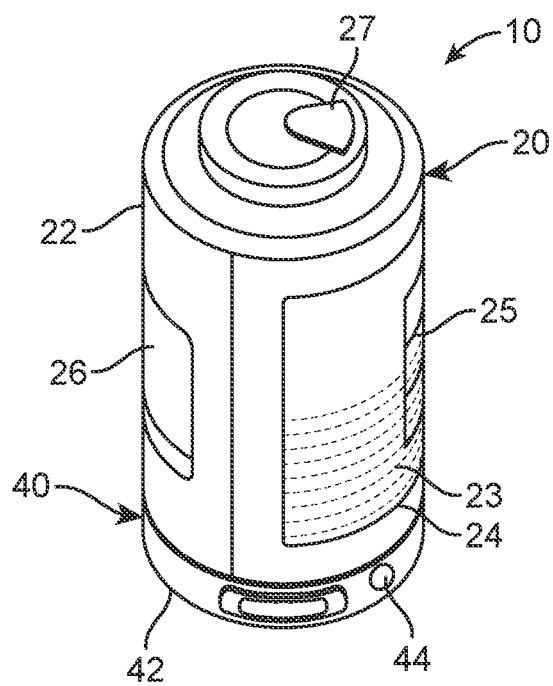
FIG. 2 shows an isometric view of room disinfecting fogger system 10 showing housing assembly 20 coupled to base assembly 40 in accordance to an embodiment of the present invention.

Container assembly 20 includes a container 22 having a substantially cylindrical configuration as depicted in FIG. 2 of the provided drawings. In can be observed that the container 22 maintains a cylindrical shape which is beneficial to the system when the container 22 is in a rotating motion. In one embodiment, container 22 may be made of a plastic or aluminum metal material. Additionally, container 22 is a sealed container which holds a disinfectant fluid 23 therein. The sealed structure of container 22 prevents any contamination from entering the container and thereby compromising the disinfectant fluid that is stored therein.

In the present embodiment, disinfectant fluid 23 is provided as a disinfectant fogging solution which, when dispersed through the container 22 transforms into a gaseous fog state. This will allow the disinfectant solution to reach and cover a wider area of the room for which it is placed in. As a result, disinfectant fluid 23 is of a dilutable formulation type. In the present embodiment, disinfectant fluid 23 is of a variety that distinctly targets the human corona virus or SARS-CoV-2. Furthermore, the present embodiment features disinfectant fluid 23 having an active ingredient of hydrogen peroxide and peracetic acid or quaternary ammonium. However, another embodiment may feature the fluid 23 as having sodium hypochlorite as the active ingredient. In yet another embodiment, the active ingredients may be featured as n-Alkyl (50% $C_{14}$, 40% $C_{12}$, 10% $C_{16}$) dimethyl benzyl ammonium saccharinate having 0.10% concentration by weight, ethanol having 58% concentration by weight, and other ingredients having a 41.90 concentration by weight.

Container 22 further includes a transparent window 24 which is featured along the sidewall of the cylindrical container. Transparent window 24 may be made of a transparent plastic or glass material. In one embodiment, transparent window 24 only partially covers the sidewalls of container 22. In another embodiment, transparent window 24 may entirely encompass the sidewalls of container 22. Furthermore, transparent window may be furnished with an indicator 25 which displays to a user the amount of fluid 23 stored within the container. In one embodiment, indicator 25 is a fill line etched into the transparent window to allow a user to observe the level of the fluid 23 therein. In another embodiment, indicator 25 is provided as indicator lights mounted to the transparent window 24. The indicator lights then are actuated depending on the amount of fluid remaining in the container. In one implementation, an indicator light is actuated when the container 22 is completely filled with fluid. In another implementation, the indicator light is actuated when container 22 is only half full of fluid. In yet another implementation, indicator light is actuated when container 22 is completely empty of fluid 23. Container 22 further comprises a fill port 26 positioned along the sidewalls of container 22. In one embodiment, fill port 26 is provided as a hinged door which swings outwardly to provide access to an interior portion of the container 22. In one embodiment, fill port 26 is a rectangular door which fits flush with the sidewalls of container 22 when the door is in a closed position.

Figure 3:
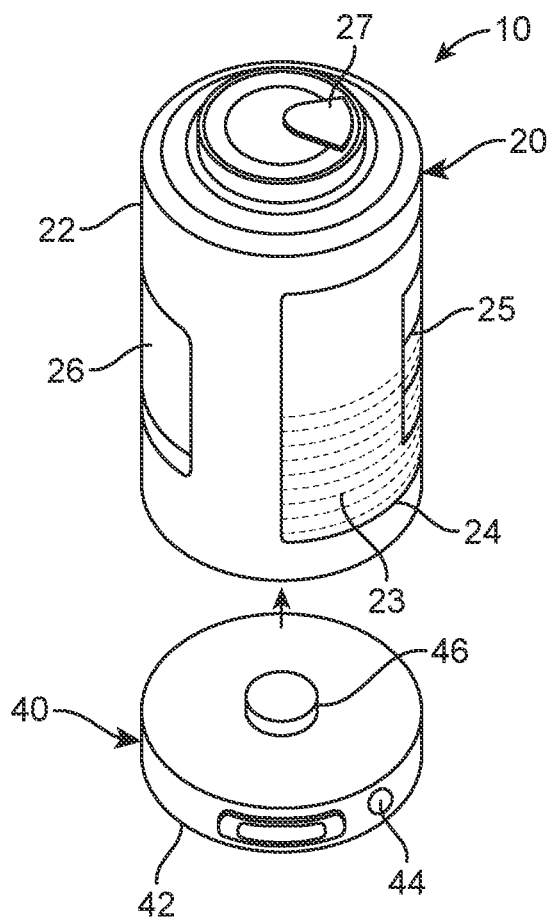
FIG. 3 illustrates an exploded view of room disinfecting fogger system 10 depicting housing assembly 20 removed from base assembly 40 in accordance to an embodiment of the present invention.
Figure 4:
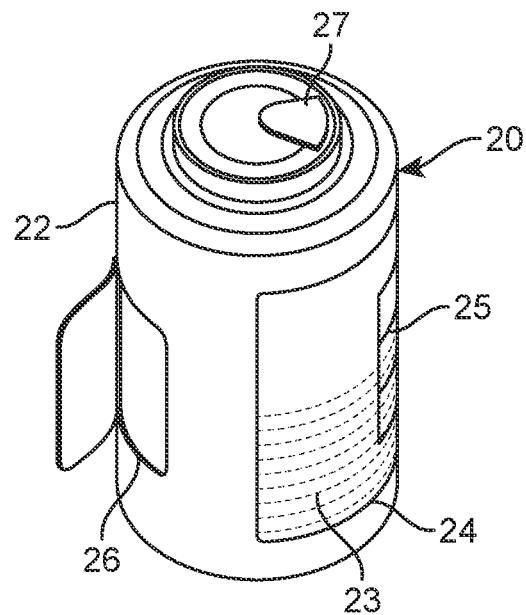
FIG. 4 is a representation of an isometric view of housing assembly 20 with fill port 26 in an open position in accordance with an embodiment of the present invention.

Housing assembly 20 further includes a motorized nozzle 27 as observed in FIGS. 2-4 of the drawings. In the present embodiment, motorized nozzle 27 dispenses the fluid 23 from within the container 22. When the fluid is dispensed from the nozzle, the fluid 23 is converted to a gaseous state due to the pressure received from the motorized nozzle 27. The gaseous solution is then dispensed in a surrounding area to effectively disinfect the area. In one implementation, motorized nozzle 27 is programmed to be dispensed in predetermined intervals. These intervals may vary from every 30 minutes, every 45 minutes, to every 1 hour. In alternate embodiments, the housing assembly 20 includes controls allowing a user to set their own custom interval into the system. In yet another embodiment, motorized nozzle 27 is coupled to a wireless communication module which allows a user to program the nozzle remotely from a mobile device. In one embodiment, depicted in FIG. 1, the gaseous solution is dispensed directly from the top end of the container 22. In another embodiment, the gaseous solution is dispensed upwardly at an angle to ensure that a wider area of the room is covered when the gas is dispensed. In yet another embodiment of the invention, the gaseous solution is dispensed horizontally from the sidewalls of container 22. The dispensing location may be set depending on the preferences of a user.

Figure 5:
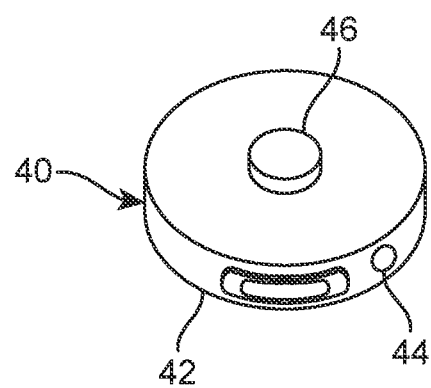
FIG. 5 shows an isometric view of base assembly 40 depicting rotating swivel 46 in accordance with an embodiment of the present invention.

Base assembly 40 includes a base 42 having a substantially circular shape as observed in FIG. 5. In can be observed that base 42 has a circular shape which corresponds to the bottom end of container 22. This is to keep uniformity and allow the system 10 to fit in most places when positioned in an area. Further, base 42 is a battery powered rotating base contain a battery 44 therein. One embodiment, battery 44 are lithium replaceable batteries which power the system for a predetermined amount of time. In another embodiment, the battery 44 is a rechargeable battery that is powered through an external port on the housing. In yet another embodiment, battery 44 is a wireless charging battery which allows a user to wirelessly charge the battery by using a wireless charger. Base 42 further includes a top end having a rotating swivel 46. In the present embodiment, the rotating swivel 46 is coupled to the bottom end of container 22 and allows it to rotate freely. Battery 44 then powers the swivel 46 to then effectively rotate the container.

In one embodiment, container 22 is in a constant rotation and dispenses the gaseous disinfectant in predetermined intervals as previously discussed. In another embodiment, container 22 is in a predetermined rotational state that may be programmed by a user. In this embodiment, the predetermined rotational state may correspond to the predetermined intervals of the motorized nozzle 27. In another embodiment, container 22 includes external controls which allow a user to input custom rotational durations. In yet another embodiment, base assembly 40 is coupled to a wireless communication module allowing a user to wirelessly program the rotational motion from a mobile device.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A disinfectant fog dispensing system, comprising:
   a. a container assembly including a cylindrical container with a top chamfer edge, wherein on a top edge of said container includes a cylindrical protruding shape, said container has a transparent window for viewing the amount of fluid within said cylindrical container, said transparent window includes an indicator, wherein said indicator emits light in accordance with the level of said fluid, said cylindrical container further including a fill port on a side of said cylindrical container, said fill port is a hinge door placed in a portion of a curved surface of said container, said cylindrical container further containing a disinfectant dilutable fluid therein, said container assembly further including a motorized nozzle for dispensing said disinfectant dilutable fluid as a gaseous disinfectant, said motorized nozzle is configured to dispense automatically said disinfectant dilutable fluid in a predetermined period, wherein said motorized nozzle is configured to dispense said disinfectant dilutable fluid upwardly and dispersed to a surrounding ambiance; and
   b. a base assembly including a base removably attachable to a bottommost edge of said container, said base has rotational motion, wherein said rotational motion is powered by means of a battery operatively connected to said base, said base having a cylindrical shape with a circumference that matches with a circumference of said container, said base will rotate and dispense said gaseous disinfectant into an enclosed area.

2. The disinfectant fog dispensing system of claim 1 wherein said disinfectant dilutable fluid includes a disinfectant fluid against SARS-CoV.

3. The disinfectant fog dispensing system of claim 1 wherein said disinfectant dilutable fluid includes quaternary ammonium as an active ingredient.

4. The disinfectant fog dispensing system of claim 1 wherein said disinfectant dilutable fluid includes sodium hypochlorite as an active ingredient.

5. The disinfectant fog dispensing system of claim 1 wherein said disinfectant dilutable fluid includes dimethyl benzyl ammonium saccharinate as an active ingredient.

6. The disinfectant fog dispensing system of claim 1 wherein said indicator are light indicators which are actuated at full, halfway, and empty levels of said cylindrical container.

7. The disinfectant fog dispensing system of claim 1 wherein said base has in a top edge thereof a cylindrical protrusion, thereby creating a rotating swivel, wherein said rotating swivel is configured to receive said container, wherein said cylindrical protrusion has said rotational motion.

8. A disinfectant fog dispensing system, comprising:
   a. a container assembly including a cylindrical container with a top chamfer edge, wherein a top edge of said container includes a cylindrical protruding shape, said container has a transparent window for viewing the amount of a fluid within said cylindrical container, said transparent window includes an indicator, wherein said indicator is a strip of emitting lights placed along the height of said transparent window, wherein said strip of emitting light is actuated in accordance with a level of said fluid, thereby said strip of emitting light illustrates a full, halfway, and empty level, said cylindrical container further including a fill port on a side of said cylindrical container, said fill port is a hinge door placed in a portion of a curved surface of said container, said fill port closes, wherein said disinfectant dilutable fluid includes an active ingredient selected from a group consisting essentially of, hydrogen peroxide and peracetic acid, quaternary ammonium, or sodium hypochlorite, said container assembly further including a motorized nozzle for dispensing said disinfectant dilutable fluid as a gaseous disinfectant placed on top of said cylindrical protruding shape, said motorized nozzle is configured to dispense automatically said disinfectant dilutable fluid in a predetermined period, wherein said motorized nozzle is configured to dispense said disinfectant dilutable fluid upwardly and dispersed to a surrounding ambiance; and
   b. a base assembly including a base removably attachable to a bottommost edge of said container, said base has rotational motion, wherein said rotational motion is powered by means of a battery operatively connected to said base, said base having a cylindrical shape with a circumference that matches with a circumference of said container, said base will rotate and dispense said gaseous disinfectant into an enclosed area, said base further includes a port on a curved surface thereof, wherein said port is operatively connected to said battery, thereby said battery is recharged by connecting said base to an external power supply.

9. A disinfectant fog dispensing system, consisting:
   a. a container assembly including a cylindrical container with a top chamfer edge, wherein a top edge of said container includes a cylindrical protruding shape, said container has a recess in a bottommost edge thereof, wherein said recess has a circular shape, said container has a transparent window for viewing the amount of a fluid within said cylindrical container, said transparent window includes an indicator, wherein said indicator is a strip of emitting lights placed along the height of said transparent window, wherein said strip of emitting light is actuated in accordance with a level of said fluid, thereby said strip of emitting light illustrates a full, halfway, and empty level, said cylindrical container further including a fill port on a side of said cylindrical container, said fill port is a hinge door placed in a portion of a curved surface of said container, said fill port closes wherein said disinfectant dilutable fluid includes an active ingredient selected from a group consisting essentially of, hydrogen peroxide and peracetic acid, quaternary ammonium, or sodium hypochlorite, said container assembly further including a motorized nozzle for dispensing said disinfectant dilutable fluid as a gaseous disinfectant placed on top of said cylindrical protruding shape, said motorized nozzle is configured to dispense automatically said disinfectant dilutable fluid in a predetermined period, wherein said motorized nozzle is configured to dispense said disinfectant dilutable fluid upwardly and dispersed to a surrounding ambiance; and
   b. a base assembly including a base removably attachable to the bottommost edge of said container, said base has a protrusion on a top edge thereof, wherein said protrusion has a rotational motion, thereby creating a rotating swivel, said rotating swivel is configured to fit into said recess, thereby said rotating swivel conveys said rotational motion to said container, wherein said rotational motion is powered by means of a battery operatively connected to said base, said base having a cylindrical shape with a circumference that conforms with a circumference of said container, said base will rotate and dispense said gaseous disinfectant into an enclosed area, said base further includes a port on a curved surface thereof, wherein said port is operatively connected to said battery, thereby said battery is recharged by connecting said base to an external power supply.

* * * * *